United States Patent [19]

Sweitzer

[11] 4,299,214
[45] Nov. 10, 1981

[54] CUFF FOR THE RELIEF OF TENNIS ELBOW AND THE LIKE

[76] Inventor: Robert R. Sweitzer, 135 N. Syndicate Ave., Thunder Bay, Ontario, Canada, P7C 3V3

[21] Appl. No.: 111,692
[22] Filed: Jan. 14, 1980
[51] Int. Cl.³ .............................................. A61F 13/00
[52] U.S. Cl. .................................................. 128/165
[58] Field of Search .................... 128/165, 77, 95, 96, 128/327; 273/189 R, 189 A, 291; 264/222

[56] References Cited

U.S. PATENT DOCUMENTS 3,970,081 7/1976 Applegate, Jr. ................ 128/165 X
4,128,097 12/1978 Bilinsky et al. .................... 128/165
4,182,318 1/1980 Beige et al. ......................... 128/165

Primary Examiner—John D. Yasko
Attorney, Agent, or Firm—Stanley G. Ade

[57] ABSTRACT

A semi-rigid formed shape or cuff is provided with a substantially U-shaped inwardly extending projection so that when wrapped around the forearm adjacent the elbow crease, controlled application of pressure is provided over the proximal area of the forearm extensor muscle group and/or the proximal forearm flexor group without applying a circumferential and equal pressure to the entire area.

8 Claims, 7 Drawing Figures

CUFF FOR THE RELIEF OF TENNIS ELBOW AND THE LIKE

BACKGROUND OF THE INVENTION

This invention relates to new and useful improvements in the design and fabrication of a brace or orthosis, referred to as a cuff or sleeve, which is to be used in the treatment of tennis elbow, either medial or lateral. Tennis elbow includes the painful condition known as epicondylitis and epicondylalgia.

Current methods of applying an external force to the lateral or medial area of the proximal forearm in order to relieve the stress imposed on the tender area of the muscle and/or the ligamentous attachment during activity, is to use a fabric band of approximately 2 inches in width which is circumferentially wrapped around the forearm and closed with a pressure sensitive fastener such as Velcro. Such bands are disclosed in J Bone Joint Surg 53A, page 183-184, 1971 by Froimson.

However such bands, although they often effect some relief, tend to dislocate on the forearm and may be foam rubber lined to prevent this. Such bands, in order to be effective, have to be relatively tight thereby tending to cause venous congestion and edema if worn too tightly or for too long. Therefore it is recommended that they are to be worn only for actual play or high stress producing situations.

Once present, the pain of tennis elbow can and often is present in all activities of daily living involving the use of the affected elbow. In such acute cases, the fabric band is often supplemented by anesthetic and steroid injections but these of course also have unfortunate side effects in certain patients.

SUMMARY OF THE INVENTION

The present invention overcomes disadvantages present with the use of relatively tight fabric band and in many instances avoid the use of injections.

This is because the invention does not apply a constrictive circumferential pressure but does apply a higher pressure to the required area. By having a semi-rigid or rigid plastic cuff shaped to the forearm with a U-shaped indentation, determined by the size and shape of the forearm, the required pressure can be readily applied to the localized area and maximized without constriction. This means that the cuff can be worn at all times if necessary and has not shown any need to be supplemented with injections or anesthetics in most test cases.

The pressure is applied over the proximal area of the forearm extensor muscle group and/or the proximal forearm flexor group without the application of a circumferential and equal pressure to the entire area with its associated complications and one aspect of the invention is to provide a cuff for the relief of tennis elbow and the like comprising a resilient, semi-rigid, split sleeve having a pair of longitudinally extending side edges defining an opening longitudinally of said sleeve, adjustable fastening means to detachably hold said sleeve in the closed position around the forearm of the patient, and an inwardly extending pressure pad formed in the wall of said cuff and situated to apply pressure over the proximal area of the forearm extensor muscle group and/or the proximal forearm flexor group of the patient.

Another aspect of the invention consists of the provision of a method of forming a cuff for the relief of tennis elbow and the like consisting of the steps of; applying a separator around the forearm of the patient, casting the forearm of the patient with a plaster of paris bandage or the like, indenting the bandage before same sets in a substantially triangular form on either side of the radial head and directly over the muscle belly overlying the radius, maintaining the pressure forming the indentations until the plaster of paris bandage has set, removing the cast and the separator by sliding same distally from the forearm, closing one end of the cast, inserting a hollow apertured metal pipe within said cast, filling the cast with a plaster of paris mix or the equivalent, removing the original cast and separator when the filling has set, carrying a U-shape to connect the indentations formed in the filling, to a depth of the indentations and smoothing off all edges to produce a gentle transition from the surface to the base of the U-shaped indentation, engaging a fabric sleeve over the cast and over the pipe, heating a synthetic plastic sheet of suitable dimensions, to a forming temperature, hand draping the hot sheet around the cast and the metal pipe, pinching off the sheet along the anterior and distal areas and around the pipe above the aperture therein, connecting said pipe to a vacuum pump and drawing the plastic sheet tightly to the cast, and then removing the formed hollow plastic sleeve from the cast and splitting same lengthwise along the anterior seam.

Another advantage of the invention is to provide a device of the character herewithin described which is simple in construction, economical in manufacture and otherwise well suited to the purpose for which it is designed.

With the foregoing in view, and other advantages as will become apparent to those skilled in the art to which this invention relates as this specification proceeds, the invention is herein described by reference to the accompanying drawings forming a part hereof, which includes a description of the preferred typical embodiment of the principles of the present invention, in which:

DESCRIPTION OF THE DRAWINGS

In the drawings like characters of reference indicate corresponding parts in the different figures.

DETAILED DESCRIPTION

Figure 1:
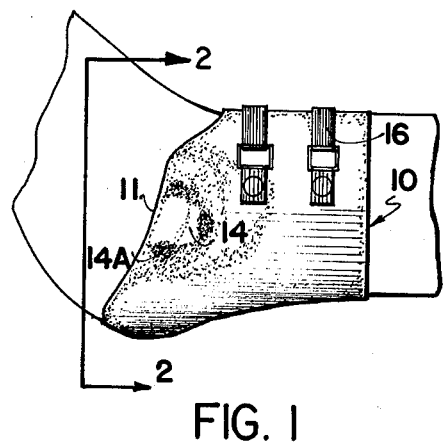
FIG. 1 is a side elevation of the finished cuff.

Proceeding therefore to describe the invention in detail, the cuff is preferably made from a polypropylene sheet of synthetic plastic. However it will be appreciated that any other suitable plastic can be used and that the finished cuff, due to the configuration thereof is relatively rigid so that the term "semi-rigid" is meant to embrace any mouldable material, which when in its finished shape, has a substantially rigid characteristic.

Dealing first with the preferred embodiment illustrated in FIGS. 1 and 2, the method of manufacture of the cuff 10 is as follows:

The patient's forearm (not illustrated) is cast with a plaster of paris bandage after the installation of a separator such as a cotton stockinette separator. The cast extends from four inches proximal to the olecranon, to approximately four inches distal to the olecranon.

During the casting process, the patient must have the forearm musculature relaxed with the elbow being flexed to approximately 90° and the hand pronated.

After the cast application but before same has set, the finger tips of the applicator's hand are pressed in triangular form so as to apply pressure on either side of the radial head and immediately distal to and directly over the muscle belly overlying the radius and this pressure is maintained until the cast has set.

Once set, the stockinette separator is reflected down over the cast and the cast and the separator removed by sliding same distally from the forearm.

Following removal of the cast, one end of the cast is closed and the cast is filled with a plaster of paris mixture or the equivalent. At this stage a hollow metal pipe is inserted into the plaster mix and the mix is allowed to harden.

Once hardened, the original plaster of paris bandage wrap is removed together with the separator and the resulting hardened cast is smoothed overall. A U-shape is carved in the cast connecting the three indentations made in the casting procedure and this carving is to a depth approximately the depth of the indentations. All edges are then smoothed off to provide a gentle transition from the normal arm shape to the base of the U-shaped indentation.

One or more small holes is now drilled in the hollow pipe as near to the cast as possible and a fabric such as a cotton stockinette or nylon stockinette is fitted over the cast snugly ensuring that this covers the drill hole or holes in the pipe.

A sheet of synthetic plastic of suitable dimension is heated and although many types of synthetic plastic can be used, it has been found that a polypropylene sheet of approximately ⅛ of an inch thickness is suitable. When heated to the forming temperature (which varies with the type of plastic sheet being used) the sheet is hand draped over the cast and the plastic is pinched together along the anterior and distal areas. It is also pinched off around the metal pipe above the drill hole with the drill hole then being connected to a vacuum pump (not illustrated) in order to draw the plastic tightly around the cast.

After the plastic sheet has cooled, the vacuum is removed and the plastic cylinder is removed from the cast. The plastic cylinder or cuff is split lengthwise along either side of the anterior seam and is then trimmed so that it is approximately 2 inches long anteriorly and 3½ inches long posteriorly.

Figure 2:
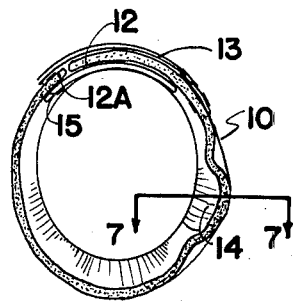
FIG. 2 is an end view thereof along the line 2—2 of FIG. 1.
Figure 3:
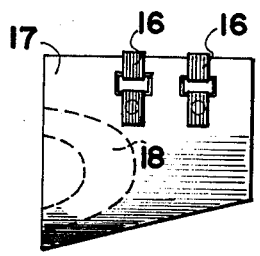
FIG. 3 is a side elevation of a cuff with a separate pressure pad.

This produces a cuff as illustrated in FIGS. 1 and 2 with the inner end 11 being shaped as shown although this is not critical.

The result is a split sleeve of somewhat resilient material having a pair of longitudinally extending side edges 12 and 12A defining the slit 13 therebetween.

The pressure pad 14 is formed on the interior surface as illustrated due to the fact that the plastic sheet was drawn into configuration upon the cast, by the vacuum pump.

A flexible leather or plastic tongue 15 is secured as by adhesive to the underside of one edge 12A of the slit and underlies the opposite side when in the closed position illustrated in FIG. 2.

Fastening means are provided and preferably take the form of Velcro strap assemblies 16 secured by adhesive or other means to the outside of the sleeve and on either side of the slit 13 and these cooperate together to pull the sleeve around the forearm of the wearer to the required degree of tightness and permitting easy release of the sleeve when necessary.

The configuration of the inner end 11 defines the location of the sleeve upon the forearm of the wearer adjacent the upper end thereof with the U-shaped portion 14 of the pressure pad fitting directly over the proximal extensor or flexor muscle group on the lateral or medial side of the proximal forearm respectively. The central area 14A of the pad is not depressed thus preventing impingement upon the humeral epicondyle when installed. The amount of pressure exerted through the pad is adjustable through the Velcro closure straps 16 located across the anterior opening or slit 13 of the cuff. By forming the cuff precisely to the forearm shape with indentations where pressure is required to relieve muscle pull on the tender area, the pressure is applied more directly and effectively.

FIG. 13 shows a conventional forearm sleeve 17 such as that referred to in Froimson above "Treatment of Tennis Elbow with Forearm Support Band" J Bone Joint Surg 53A, page 183–184, 1971.

Figure 4:
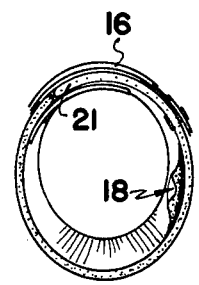
FIG. 4 is an end view of FIG. 3 showing the separate pressure pad attached to the interior wall of the cuff.
Figure 5:
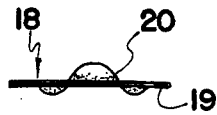
FIG. 5 is a side view of the separate pressure pad per se.
Figure 6:
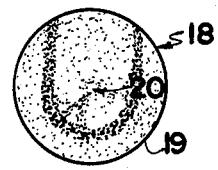
FIG. 6 is a plan view of FIG. 5.
Figure 7:
FIG. 7 is a fragmentary cross sectional view along the line 7—7 of FIG. 2.

The use of this particular cuff can be improved by the application of a pressure pad separate from the cuff as indicated by reference character 18 and illustrated in FIGS. 5 and 6. This may take the form of a cylindrical base portion 19 with the pressure pad 20 formed thereon and this may be adhesively secured to the inner surface 21 of the cuff 17 as shown in FIG. 4. It should be noted that the upper or proximal portion is not intended therefore preventing impingement upon the humeral epicondyle.

Use of the pressure paid in this type of cuff provides added benefit to the device and the inserts 20 could be made of any semi-rigid or rigid material.

The cuff hereinbefore described is preferably made from a polypropylene sheet which is semi-rigid. However the inherent shape of the pad with the compound curves makes that particular area, rigid. And similar materials could be used for the separate pressure pads 18.

Finally, it should be noted that the position of the cuff on the forearm should be such that the cuff should not extend more than two inches distally from the anterior surface of the upper arm otherwise active muscle contraction will create severe discomfort.

Since various modifications can be made in my invention as hereinabove described, and many apparently widely different embodiments of same made within the spirit and scope of the claims without departing from such spirit and scope, it is intended that all matter contained in the accompanying specification shall be interpreted as illustrative only and not in a limiting sense.

What I claim as my invention is:

1. A cuff for the relief of tennis elbow and the like comprising a resilient, semi-rigid, split sleeve having a pair of longitudinally extending side edges defining an opening longitudinally of said sleeve, adjustable fastening means to detachably hold said sleeve in the closed position around the forearm of the patient, and an inwardly extending pressure pad formed in the wall of said cuff and situated to apply pressure over the proximal area of the forearm extensor muscle group and/or the proximal forearm flexor group of the patient, said pressure pad being substantially U-shaped when viewed in plan with the inner surface blending smoothly into the inner surface of the sleeve, said U-shape surrounding a conical area of the wall which is not depressed thereby preventing impingement upon the humeral epicondyle of the patient.

2. The invention according to claim 1 which includes a tongue secured by one edge thereof to adjacent the inside area of one side of the opening and underline the other side of the opening.

3. The invention according to claim 1 in which said adjustable fastening means includes a pair of spaced apart, pressure sensitive, fastening straps secured by the ends thereof to the outside of said sleeve and spanning the opening therein, when closed.

4. The invention according to claim 2 in which said adjustable fastening means includes a pair of spaced apart, pressure sensitive, fastening straps secured by the ends thereof to the outside of said sleeve and spanning the opening therein, when closed.

5. The invention according to claim 1 or 2 in which the pressure pad is formed separately from the cuff and is detachably securable to the wall of the cuff in the desired position.

6. The invention according to claim 3 in which the pressure pad is formed separately from the cuff and is detachably securable to the wall of the cuff in the desired position.

7. The invention according to claim 4 in which the pressure pad is formed separately from the cuff and is detachably securable to the wall of the cuff in the desired position.

8. A method of forming a cuff for the relief of tennis elbow and the like consisting of the steps of;

(a) applying a separator around the forearm of the patient, (b) casting the forearm of the patient with a plaster of paris bandage or the like, (c) indenting the bandage before same sets in a substantially triangular form on either side of the radial head and directly over the muscle belly overlying the radius, (d) maintaining the pressure forming the indentations until the plaster of paris bandage has set, (e) removing the cast and the separator by sliding same distally from the forearm, (f) closing one end of the cast, (g) inserting a hollow apertured metal pipe within said cast, (h) filling the cast with a plaster of paris mix or the equivalent, (i) removing the original cast and separator when the filling has set, (j) carving a U-shape to connect the indentations formed in the filling, to a depth of the indentations and smoothing off all edges to produce a gentle transition from the surface to the base of the U-shaped indentation, (k) engaging a fabric sleeve over the cast and over the pipe, (l) heating a synthetic plastic sheet of suitable dimensions, to a forming temperature, (m) hand draping the hot sheet around the cast and the metal pipe, pinching off the sheet along the anterior and distal areas and around the pipe above the aperture therein, (n) connecting said pipe to a vacuum pump and drawing the plastic sheet tightly to the cast, (o) and then removing the formed hollow plastic sleeve from the cast and splitting same lengthwise along the anterior seam.

* * * * *